United States Patent
Fournier et al.

(10) Patent No.: US 9,819,103 B2
(45) Date of Patent: Nov. 14, 2017

(54) WASHABLE INTELLIGENT GARMENT AND COMPONENTS THEREOF

(71) Applicant: CARRE TECHNOLOGIES INC., Montreal (CA)

(72) Inventors: Pierre-Alexandre Fournier, Montreal (CA); Jean-Francois Roy, Sherbrooke (CA); Charles Robillard, Saint-Lazare (CA); Stephan Gagnon, Rosemere (CA)

(73) Assignee: CARRE TECHNOLOGIES INC., Montreal (CA)

( * ) Notice: Subject to any disclaimer, the term of this patent is extended or adjusted under 35 U.S.C. 154(b) by 520 days.

(21) Appl. No.: 14/385,675

(22) PCT Filed: Mar. 12, 2013

(86) PCT No.: PCT/CA2013/000221
§ 371 (c)(1),
(2) Date: Sep. 16, 2014

(87) PCT Pub. No.: WO2013/134856
PCT Pub. Date: Sep. 19, 2013

(65) Prior Publication Data
US 2015/0047091 A1   Feb. 19, 2015

Related U.S. Application Data

(60) Provisional application No. 61/611,944, filed on Mar. 16, 2012.

(51) Int. Cl.
*H01R 11/01* (2006.01)
*H01R 4/58* (2006.01)
(Continued)

(52) U.S. Cl.
CPC ............. *H01R 11/01* (2013.01); *A41D 1/005* (2013.01); *H01R 4/58* (2013.01); *H01R 13/52* (2013.01);
(Continued)

(58) Field of Classification Search
CPC .................................. H01R 11/01; H01R 4/58
See application file for complete search history.

(56) References Cited

U.S. PATENT DOCUMENTS 6,305,962 B1   10/2001   Maher et al.
6,645,008 B2   11/2003   Massey et al.
(Continued)

FOREIGN PATENT DOCUMENTS

WO   2009036327 A1   3/2009
WO   2012160123 A1   11/2012

OTHER PUBLICATIONS

International Search Report of PCT/CA2013/000221; dated May 31, 2013; Jim Triantafillou.

*Primary Examiner* — James Harvey
(74) *Attorney, Agent, or Firm* — BCF LLP

(57) ABSTRACT

The present relates to a washable interconnection patch, a connection assembly, and an intelligent washable garment equipped therewith. The patch receives and interconnects wires to a cable. The patch comprises two matching pieces interlocking together so as to define there between two opposite apertures. One of the apertures is adapted to receive and hold the wires, and the other aperture is adapted to receive and hold the cable. One of the two matching pieces defines on an interior face a channel to interconnect the wires to the cables. The connection assembly comprises a male connector and a female connector. The male connector defines a series of independent connection points along a length thereof. The female connector is adapted to receive the male connector, and defines along a length of an inner (Continued)

surface thereof a series of contact points. When the male connector is inserted within the female connector, the connection points and the contact points are aligned and in contact together.

14 Claims, 18 Drawing Sheets

(51) Int. Cl.
*H02G 15/013* (2006.01)
*A41D 1/00* (2006.01)
*H01R 13/52* (2006.01)
*H01R 13/58* (2006.01)
*H02G 15/00* (2006.01)
*H02G 15/113* (2006.01)
*H01R 12/71* (2011.01)
*A61B 5/00* (2006.01)

(52) U.S. Cl.
CPC .......... *H01R 13/58* (2013.01); *H02G 15/013* (2013.01); *A61B 5/6805* (2013.01); *H01R 12/714* (2013.01); *H02G 15/003* (2013.01); *H02G 15/113* (2013.01)

(56) References Cited

U.S. PATENT DOCUMENTS

| | | | |
|---|---|---|---|
| 7,344,379 B2* | 3/2008 | Marmaropoulos | H01R 13/6205 439/37 |
| 7,476,104 B2* | 1/2009 | Marmaropoulos | A41D 27/205 439/37 |
| 8,308,489 B2* | 11/2012 | Lee | H01R 13/2407 2/69 |
| 8,529,277 B2* | 9/2013 | Williams | H01R 12/716 439/369 |
| 9,231,327 B1* | 1/2016 | Liu | H01R 13/22 |
| 9,577,374 B1* | 2/2017 | Grant | H01R 4/58 |
| 2002/0089399 A1 | 7/2002 | Massey et al. | |
| 2005/0054941 A1 | 3/2005 | Ting et al. | |
| 2006/0128169 A1* | 6/2006 | Marmaropoulos | H01R 13/193 439/37 |
| 2007/0105404 A1* | 5/2007 | Lee | H01R 12/592 439/37 |
| 2008/0015454 A1 | 1/2008 | Gal | |
| 2008/0064964 A1 | 3/2008 | Nagata et al. | |
| 2009/0099423 A1 | 4/2009 | Al-Ali et al. | |
| 2009/0306485 A1 | 12/2009 | Bell | |
| 2010/0136804 A1* | 6/2010 | Strickland | H01H 1/12 439/65 |
| 2011/0087115 A1 | 4/2011 | Sackner et al. | |
| 2015/0047091 A1* | 2/2015 | Fournier | H02G 15/013 2/69 |
| 2016/0226158 A1* | 8/2016 | Cox | H01R 4/20 |

* cited by examiner

Example of bottom contact pads on male connector for spring-loaded contacts in female connector Example of top soldering pads for electrical wires inside the male connector

| Removable Data Storage Unit | Wireless Components, Antenna | Power Management |
|---|---|---|
| Solid State Memory | Serial Protocol Components, Connector | Rechargeable Battery |
| CPU / Analog-Digital Converters ||||
| Electrocardiogram | Respiratory Inductance Plethysmograph | Thermistors Amplification | Position/ Acceleration Sensors |
| Connector to garment sensors ||||

Figure 18

WASHABLE INTELLIGENT GARMENT AND COMPONENTS THEREOF

The present relates to a washable interconnection patch, a male-female connector assembly, and a washable intelligent garment equipped with such a washable interconnection patch and male-female connector assembly.

BACKGROUND

Physiological sensors have long been known and widely used for medical and health related applications. Various physiological sensors embedded in textile or garments, sometimes called portable or wearable sensors, have been described before in publications and patents (Portable Blood Pressure, U.S. Pat. No. 4,889,132, Filing date: Sep. 26, 1986 Issue date: Dec. 26, 1989; Portable device for sensing cardiac function, U.S. Pat. No. 4,928,690, Filing date: Apr. 25, 1988, Issue date: May 29, 1990). The term "wearable sensors" is now commonly used to describe a variety of body-worn sensors to monitor activity, environmental data, body signals, biometrics, health related signals, and other types of data.

Electrocardiogram (ECG) electrodes made of conductive textile, conductive polymer, metal and other materials used in wearable sensors have been described in patents such as (Textile-based electrode, U.S. Pat. No. 7,970,451, Filing date: Dec. 31, 2008, Issue date: Jun. 28, 2011).

Textile-based Respiratory Inductive Plethysmography sensors have been described in patents such as (Method and apparatus for monitoring respiration, U.S. Pat. No. 4,308,872 Issue date: Jan. 5, 1982).

Multi-parameter wearable connected personal monitoring systems (Zephyr Technology' BioHarness, Qinetiq's Traintrak, Weartech's GOW, Nuubo's nECG) are already available on the market.

However, the single or multi-parameter systems known in the industry use clip buttons made of conductive material for connecting the textile sensors to an electronic module. These clip buttons limit the number and types of interconnections available between the electronic module and the textile sensors.

Connectivity is a domain with many technological challenges to the manufacturer of e-textile solutions, intelligent garments, wearable sensors, and multi-parameter wearable connected personal monitoring systems. There is thus a need for improved connectivity solutions, and for garments equipped with such connectivity solutions.

BRIEF DESCRIPTION OF THE DRAWINGS

In the appended drawings:

FIG. 8a is a bottom view of the PCB of the male connector showing circular electrical contacts.

FIG. 8b is a top view of the PCB of the male connector showing rectangular contacts for soldering and printed wires.

FIG. 18 shows a diagram of functional components used in the electronic device.

DETAILED DESCRIPTION

The foregoing and other features of the present garment and components thereof will become more apparent upon reading of the following non-restrictive description of examples of implementation thereof, given by way of illustration only with reference to the accompanying drawings.

Connectivity is a domain with many technological challenges for designers and manufacturers of e-textile solutions, intelligent garments, wearable sensors, and multi-parameter wearable connected personal monitoring systems.

Figure 1:
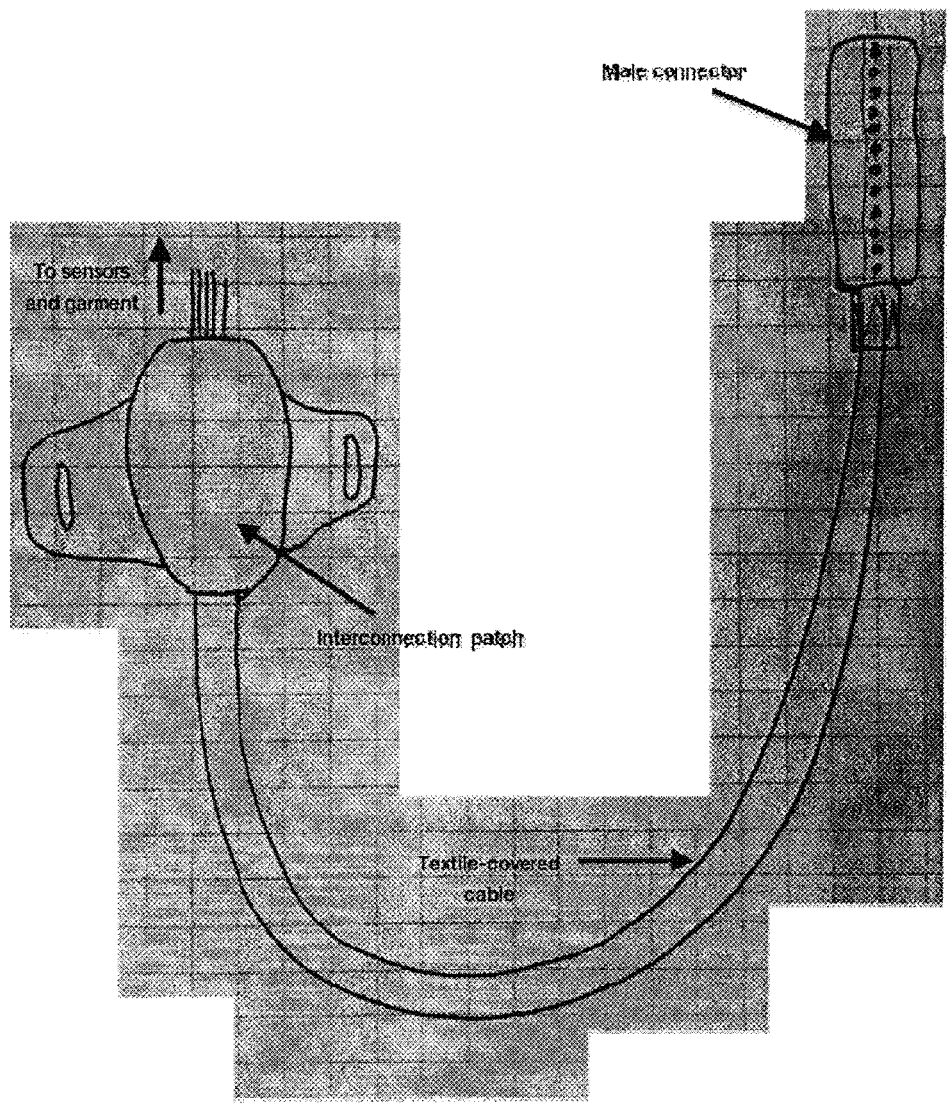
FIG. 1 is a schematic representation of an interconnection patch that can be assembled in a garment, with a textile-covered cable and a washable male connector.
Figure 2A:
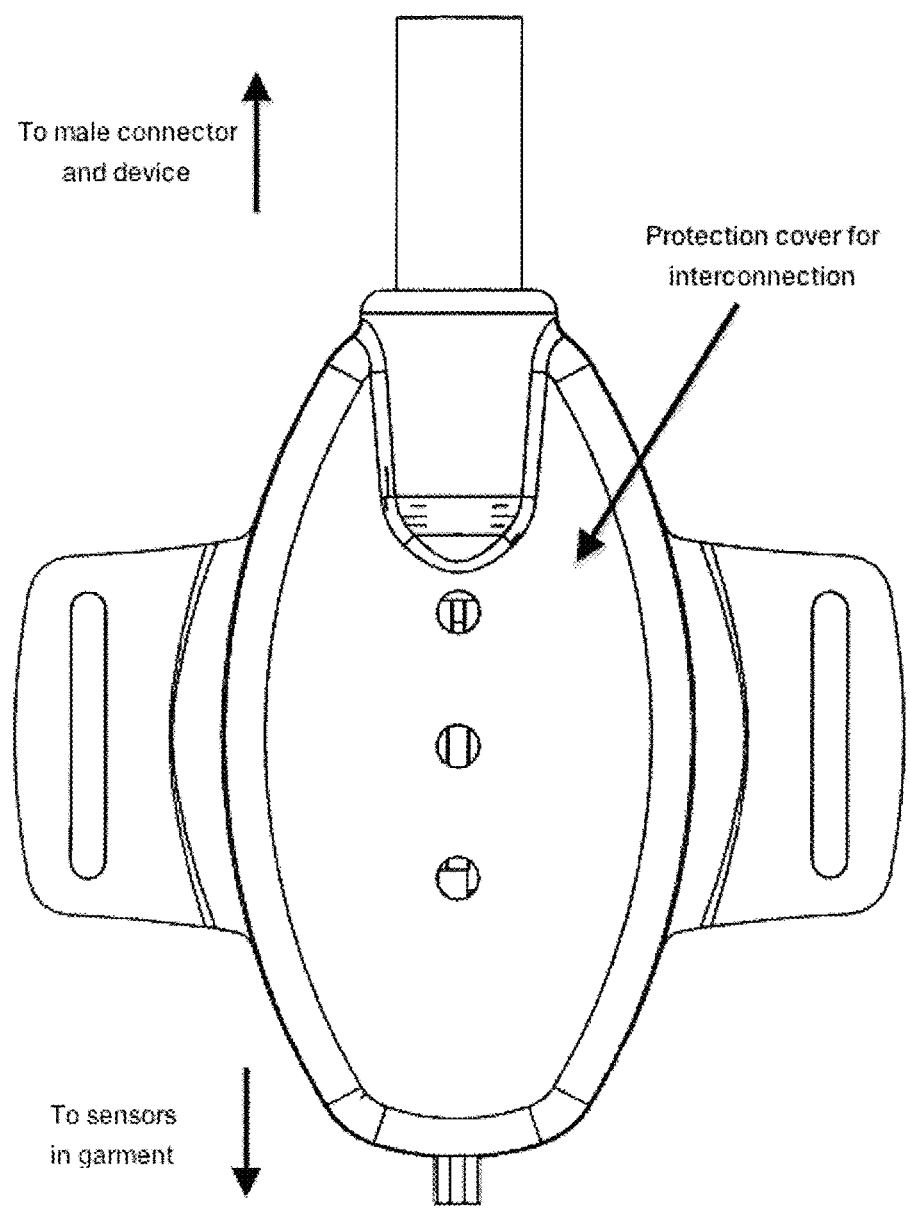
FIG. 2a is a top view of a washable interconnection patch adapted for electrical and optical interconnections.
Figure 2B:
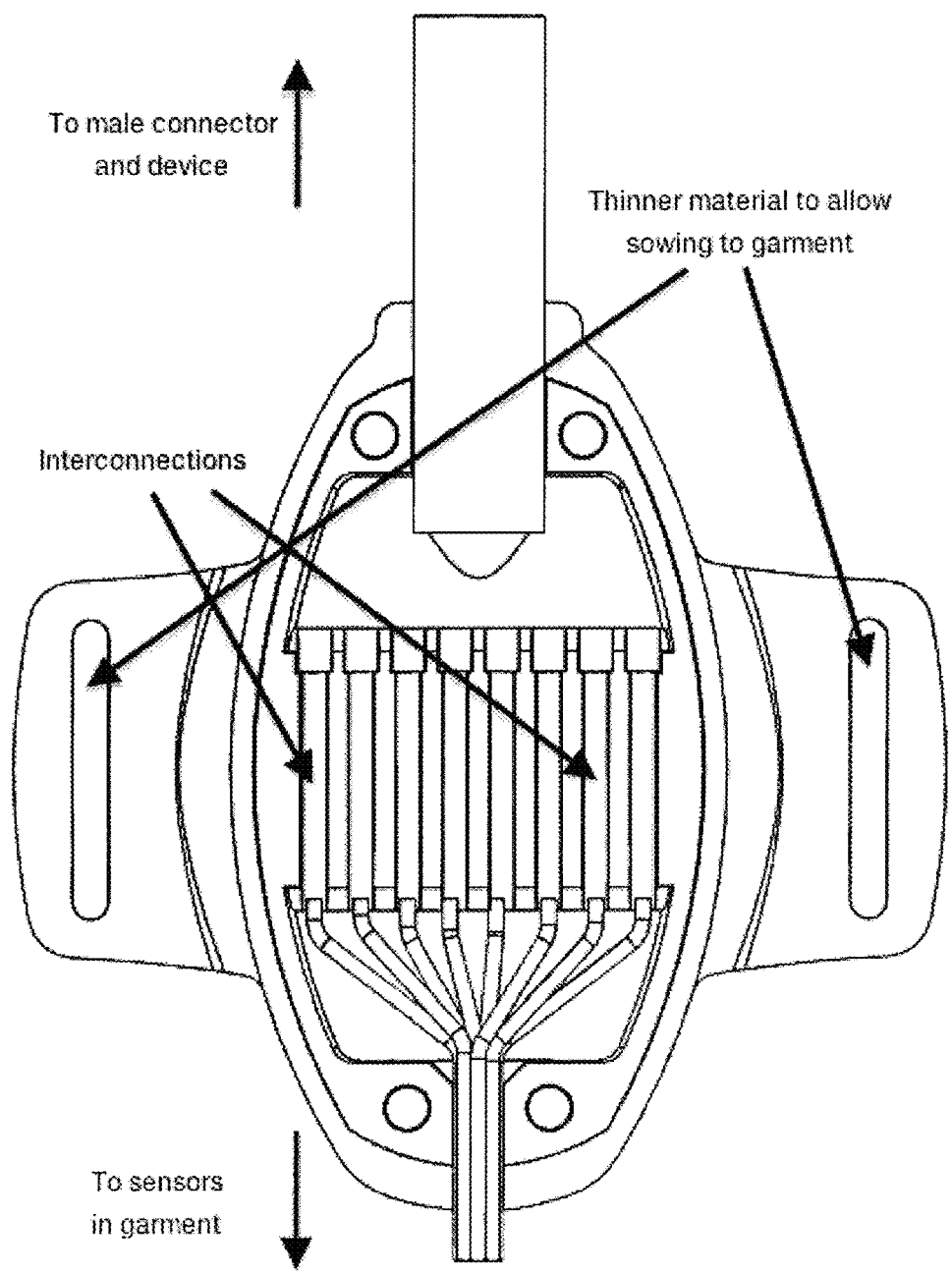
FIG. 2b is a top view of the washable interconnection patch showing wire interconnections inside the patch before encapsulation.

In an aspect, the present specification describes a washable electronic male-female connector. The male connector is designed to be attached to a washable and/or wearable sensor system (as exemplary shown in FIG. 1) and comprises a cable, which may be covered with textile, and an interconnection patch where many electric and/or optical wires can be connected to the cable as exemplary shown in FIGS. 2a and 2b. The male connector may further comprise strain relief components.

The male connector and its components can be made of various materials. In one example, the patch and strain relief components may be made of any of the following material: silicone, rubber, or another flexible material over-molded over the cable. The cable may be made of many color-coded electrical wires, bundled together using a textile fabric knitted around the wires. The male connector and strain relief components may be made using over-molded resin. In one example electrical interconnections between wires coming from the garment and the wires in the cable are made using a small open crimp or a crimp tube (as exemplary shown in FIG. 2b, and the interconnection is sealed using silicone, rubber, or any other sealing material compatible with the over-molded patch.

The interconnection patch can be made using a manufacturing process that does not require heating, for example crimps and/or glue and/or silicone with low curing temperature, which has among its advantages the benefit of reducing the risk to deteriorate or destroy heat sensitive textiles that can be used in a garment.

Figure 4:
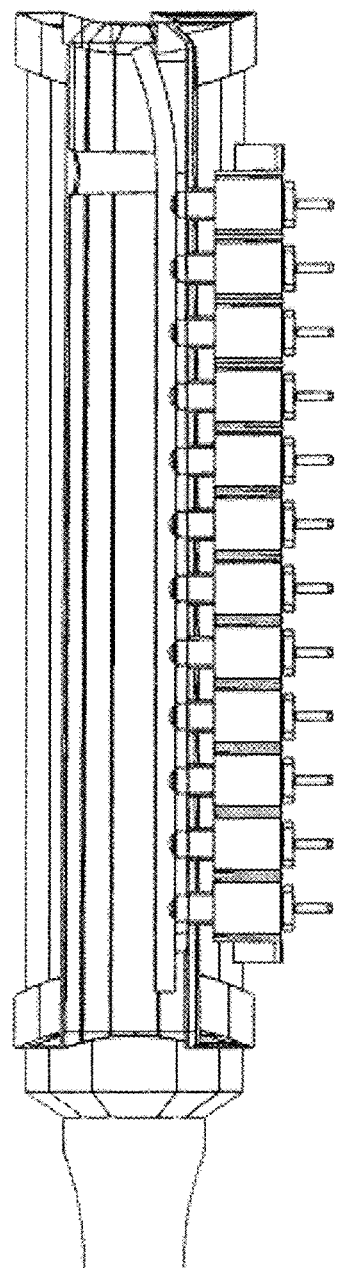
FIG. 4 is a cross-sectional view of the male and female connector, showing a curve (called "ski" or "banana") in the printed circuit board of the male connector, allowing the spring-loaded electrical pins to be put in compression without applying a side force on the pin of the female connector while inserting.
Figure 5:
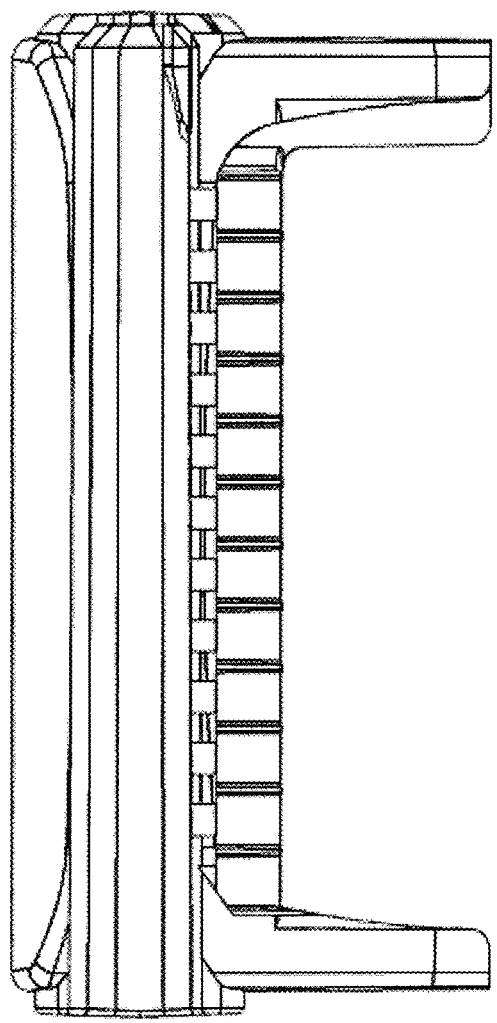
FIG. 5 is a cross-sectional view of the female connector, without the spring-loaded electrical pins.
Figure 6:
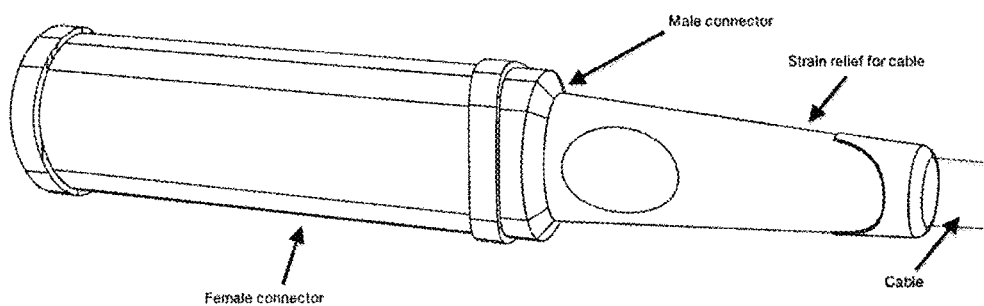
FIG. 6 is a view of the male connector assembled with a cable segment, inserted in the female connector.
Figure 8:
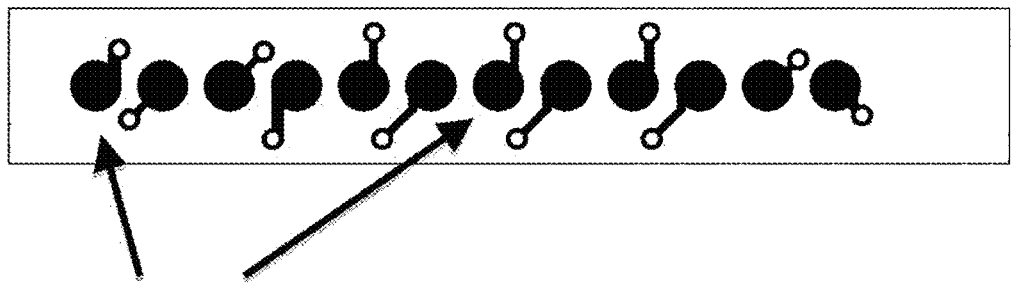
FIG. 8 is a side view of the printed circuit board (PCB) of the male connector showing the curve that pushes the spring-loaded pins during insertion.
Figure 8:
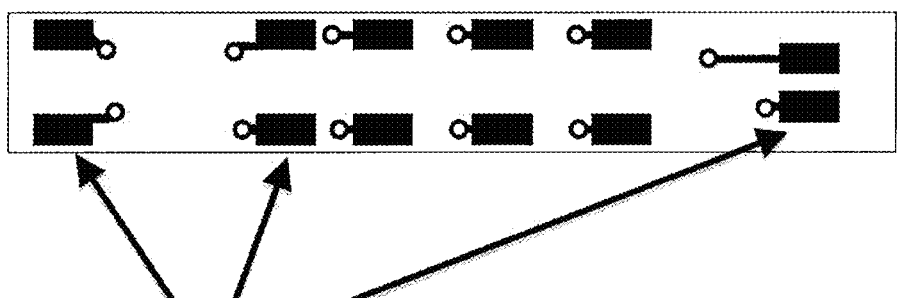
Figure 11:
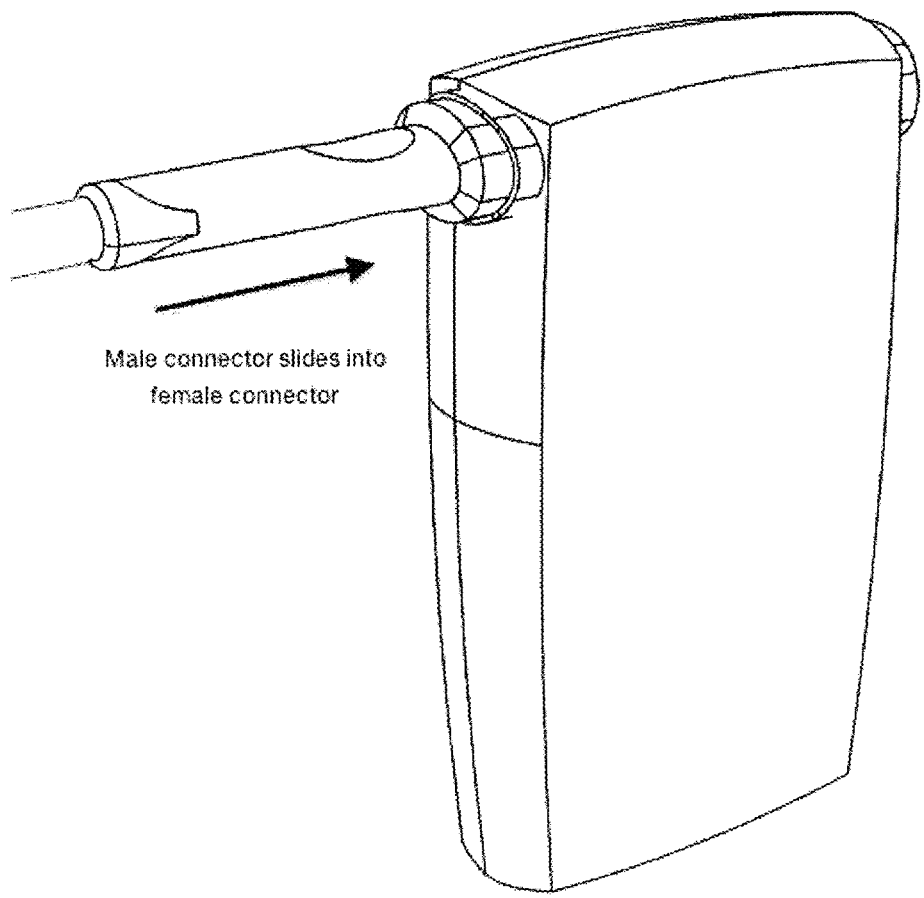
FIG. 11 is a view of the male connector and a cable segment inserted in the side of the female connector of a small electronic device.
Figure 15:
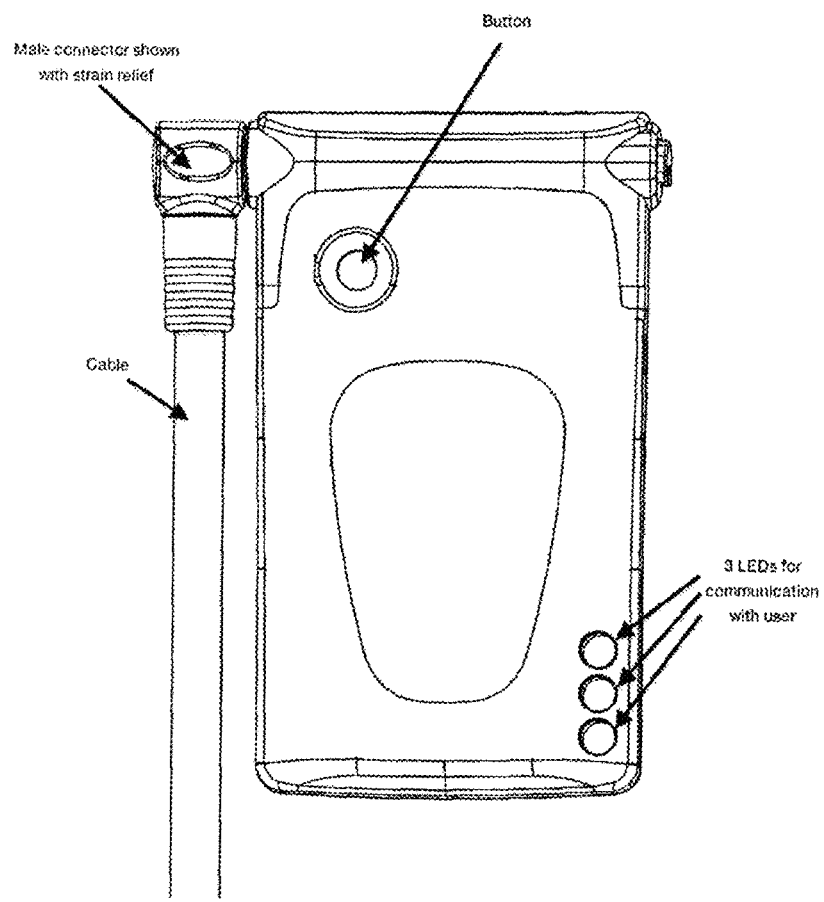
FIG. 15 shows a device that includes a female connector, connected to a cable with a right-angle male connector. The device has a button that can be used to record an event, initiate wireless pairing using a protocol like Bluetooth, or reset the device. In this example, the device has 3 light emitting diodes used to communicate with users.

In a particular embodiment, the male connector is designed with a small curve at one of its longitudinal extremity to be adapted to lower spring-loaded contacts during insertion in the female connector (see FIGS. 4 and 8). In one example, the male connector is made of a printed circuit board shaped like a ski (see FIG. 8), electronic contacts with the female connector being made when engaged with conductors printed at the bottom of the ski-shaped circuit board (FIG. 8a), while the wires are soldered on the top of the circuit board (FIG. 8b) before it is over-molded to become the male connector and the strain relief for the wires and cable connected to the washable interconnection patch. The strain relief (FIG. 11) can also be made at a right angle (FIG. 15) to make the cable follow the side of the device and reduce the space needed for the cable and device in a pocket on the garment. For example, the circuit board and cable may be overmolded in one piece to create the male connector. The strain relief is then the part of the connector attaching the cable to the plastic shell of the male connector to avoid putting tension on the soldered connection between the wires and the circuit board.

In a further embodiment, the electrical contacts on the male connector are plated with gold or another conductive material not affected by oxydation or degradation caused by air, light, water, soap, enzymes or other chemical or biological products.

Figure 3:
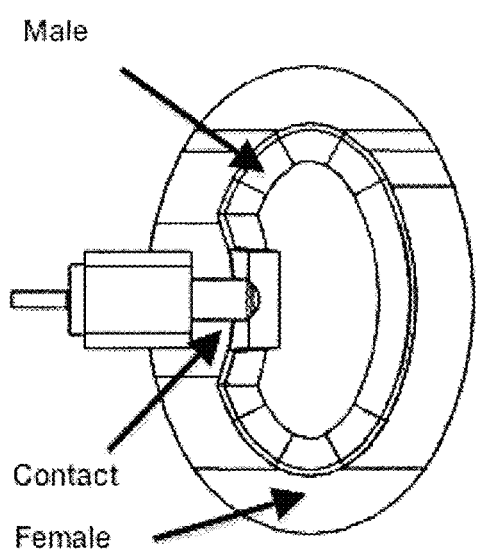
FIG. 3 is a cross-sectional side view of a male and female washable connector, showing spring-loaded electrical pins in contact with a printed circuit board of the male connector.
Figure 9:
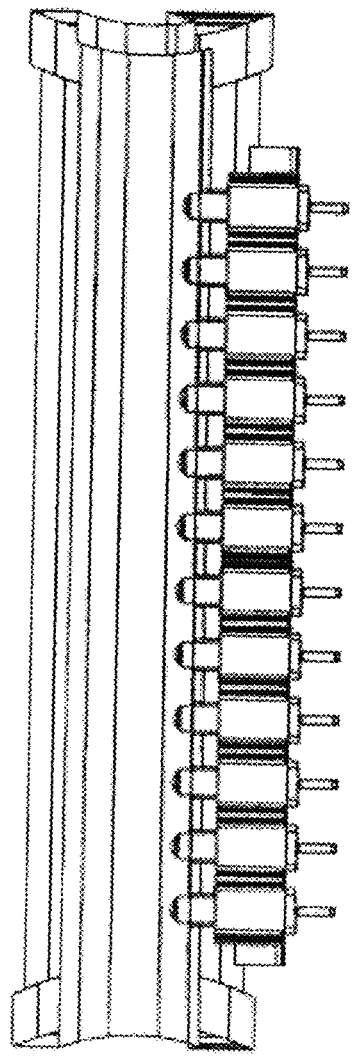
FIG. 9 is a cross-sectional view of the female connector made with standard spring-loaded contacts embedded in a plastic component and aligned with an aperture shaped like a cylinder to host the male connector.
Figure 10:
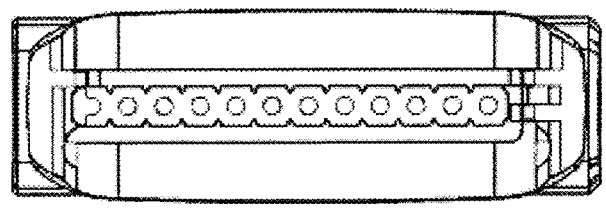
FIG. 10 is a bottom view of the plastic component of the female connector showing the shape and apertures ready to host a row of spring-loaded contacts.

The female connector may comprise spring-loaded contacts that are lined up along an aperture shaped like a cylinder (see FIGS. 4 and 9). The aperture is asymmetric to facilitate the alignment of the contacts with the contacts of the male connector (see FIG. 3). The female connector can be made as one piece including the spring-loaded contacts, or two pieces including for example one row of spring-loaded connectors and an injection molded plastic piece defining an asymmetric aperture (see FIG. 10).

Figure 7:
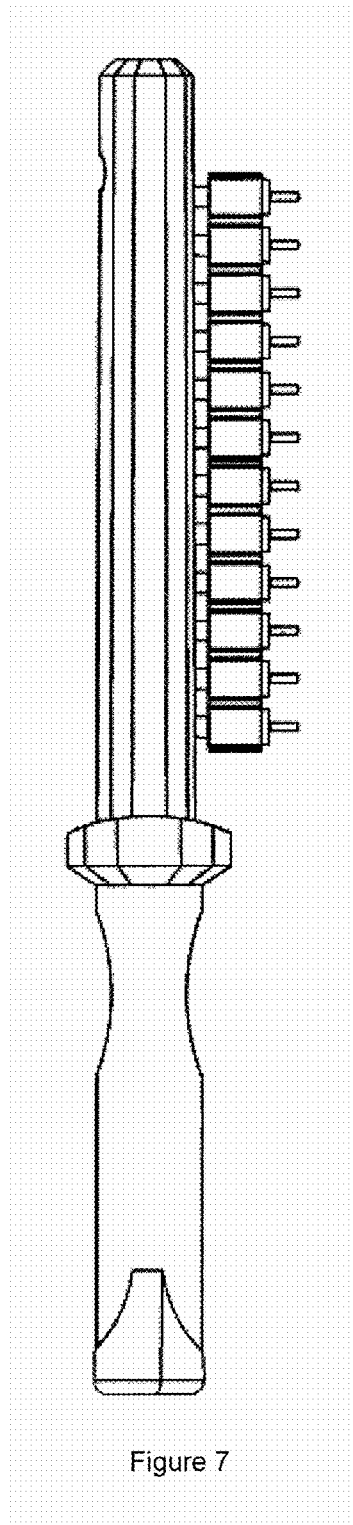
FIG. 7 is a side view of the male connector with the spring-loaded pins in contact with the printed circuit board conductive pads.

Electric and/or optic connection between the male and female connectors is completed upon complete engagement of the male connector within the female connector, which permits the contacts of the male connector to be aligned with the spring-loaded contacts of the female connector (see FIG. 7).

The device starts recording the physiological signals automatically from the sensors upon complete connection of the male connector within the female connector, and stops recording when the male connector is removed from the female connector. This feature simplifies the use of the recording device and reduces power consumption from the battery when the device is not connected.

Figure 12:
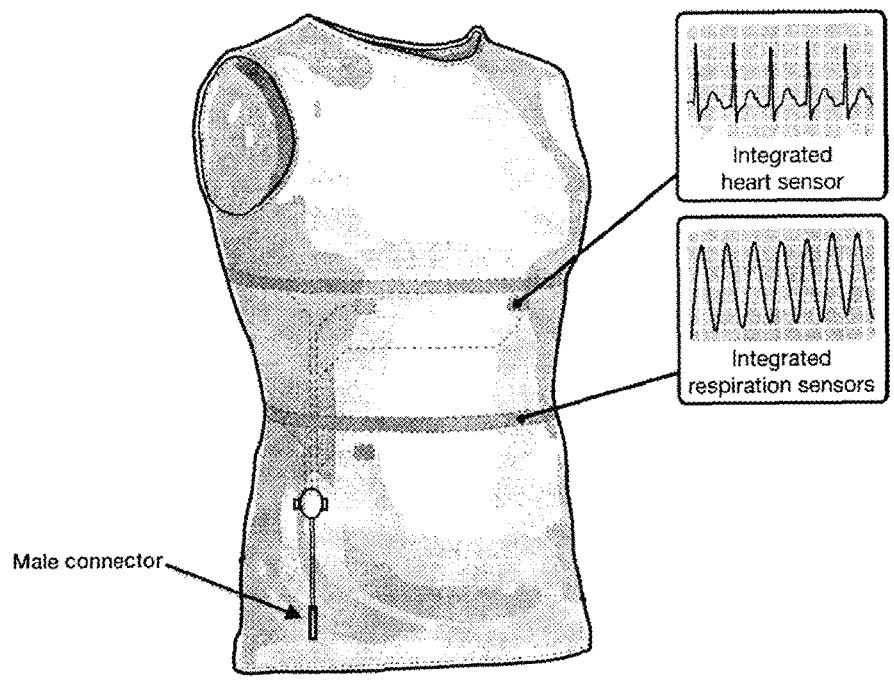
FIG. 12 is Hexoskin garment with a male connector. The garment illustrated has conductive textile electrodes and textile-based respiratory inductive plethysmography sensors connected to the interconnection patch with flexible and elastic wires.
Figure 13:
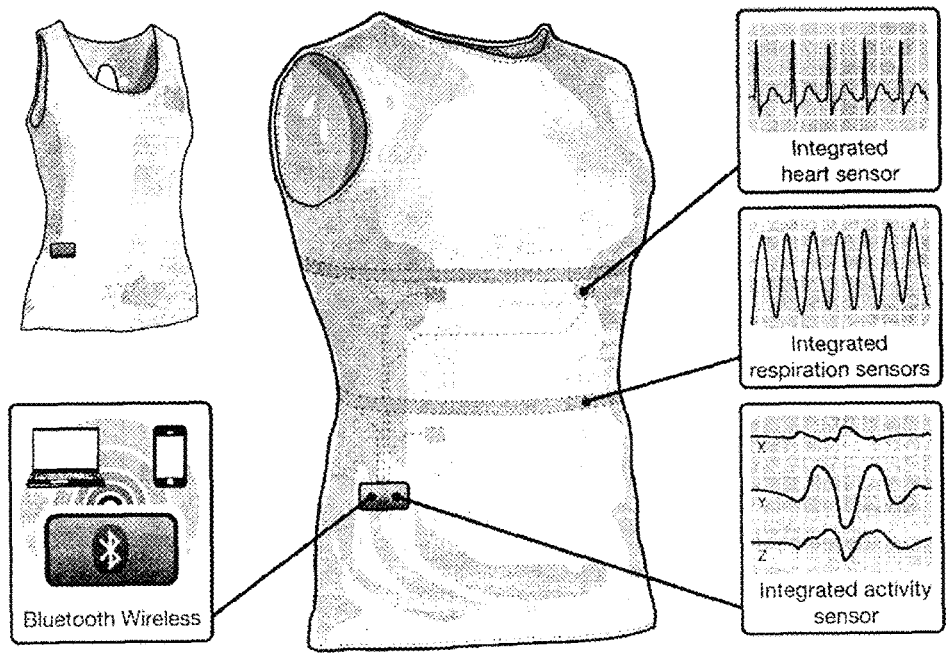
FIG. 13 shows garments that use the present patch and connection system to connect textiles sensors for heart and breathing monitoring to an electronic device with an accelerometer and a Bluetooth wireless connection. The electronic device also contains analog and digital filters and amplifiers, a microprocessor device, solid-state memory storage, sensor circuits, power management circuits, buttons, and other circuits.

An example of use of the present male-female connector and the present interconnection patch are wearable physiological monitoring garments as shown in FIGS. 12 and 13.

Figure 14:
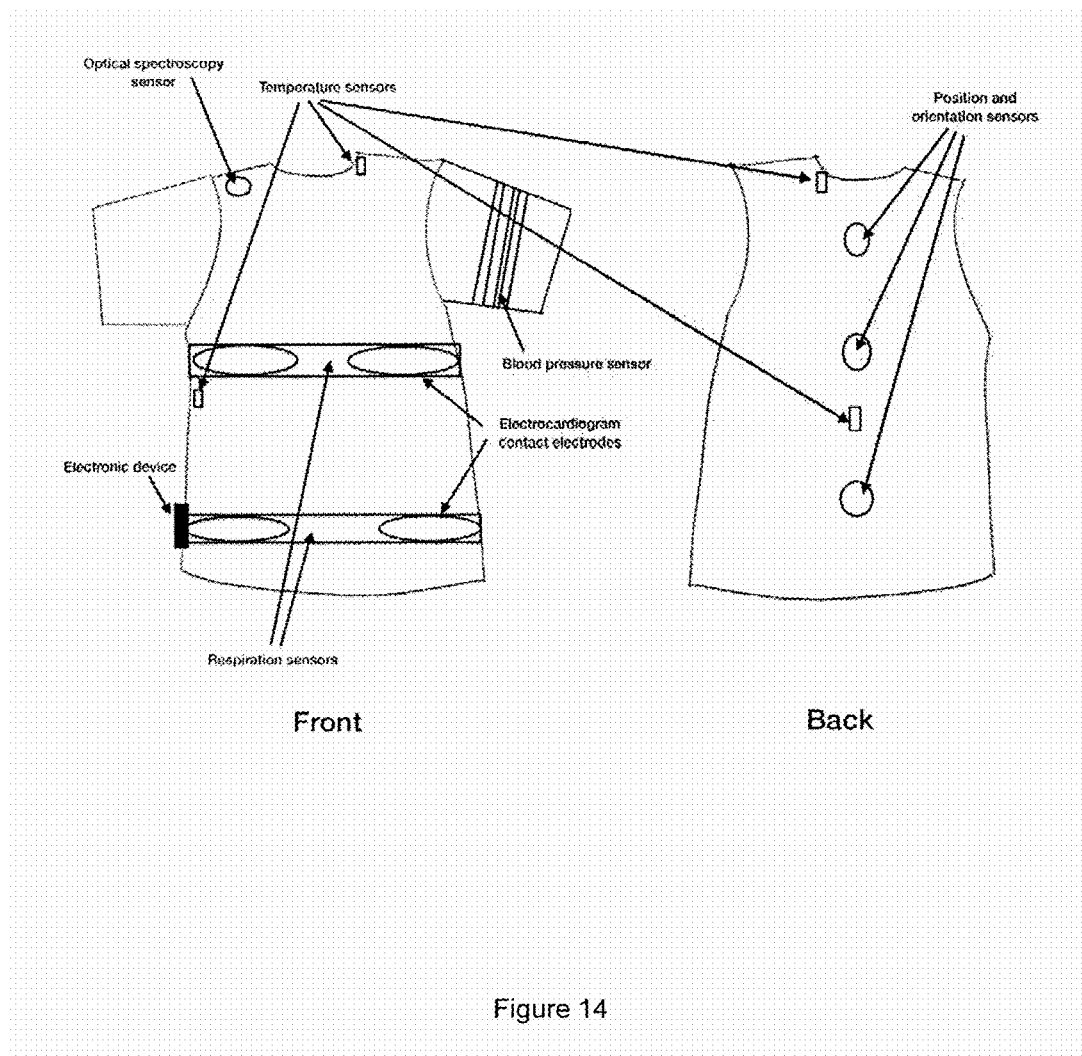
FIG. 14 shows a garment with electrical and optical sensors that use the present system to connect textiles, electrical, thermal, and optical sensors for cardiac monitoring, breathing monitoring, blood pressure monitoring, skin temperature and core temperature monitoring to an electronic device with position sensors and a wireless data connection.

Reference is now made to FIG. 14, which depicts another exemplary use of the present system, where an upper-body garment is equipped with physiological sensors to measure body activity and state with a recording, processing and transmitting wearable device that connects to physiological sensors. The garment is embedded with electrodes for electrocardiogram (ECG) or electromyogram (EMG) recordings, thermal sensors for skin temperature monitoring, multidimensional acceleration and position sensors for position and movement monitoring, microphone for heart and lung auscultation, inductance plethysmography sensors to measure changes in volume of the upper body, optical sensors for body spectrophotometry, and a blood pressure sensor on the left arm of the garment. This wearable physiological sensor system provides enhanced users' mobility compared to previous systems, allows simultaneous recording of all the aforementioned signals, allows simultaneous encoding and wireless transmission of all the aforementioned signals, allows automatic processing, analysis, and modeling of all the aforementioned signals, is less vulnerable to position and motion artifacts hence capable of producing high quality signals during sleep, running, exercising and other normal activities. The sensor system, including the present male-female connector, and the interconnection patch, is thus washable in a regular domestic washing machine. Any electronic device may be connected to the garment using the present male-female connector. The electronic device may thus be located in a pocket designed for carrying. The electronic device can communicate with mobile phones and computer devices using a wireless or wired communication protocol. When used with low height profile embedded sensors, the present system makes it possible to wear the garment during sleep, physical activity, and in other contexts.

Figure 16:
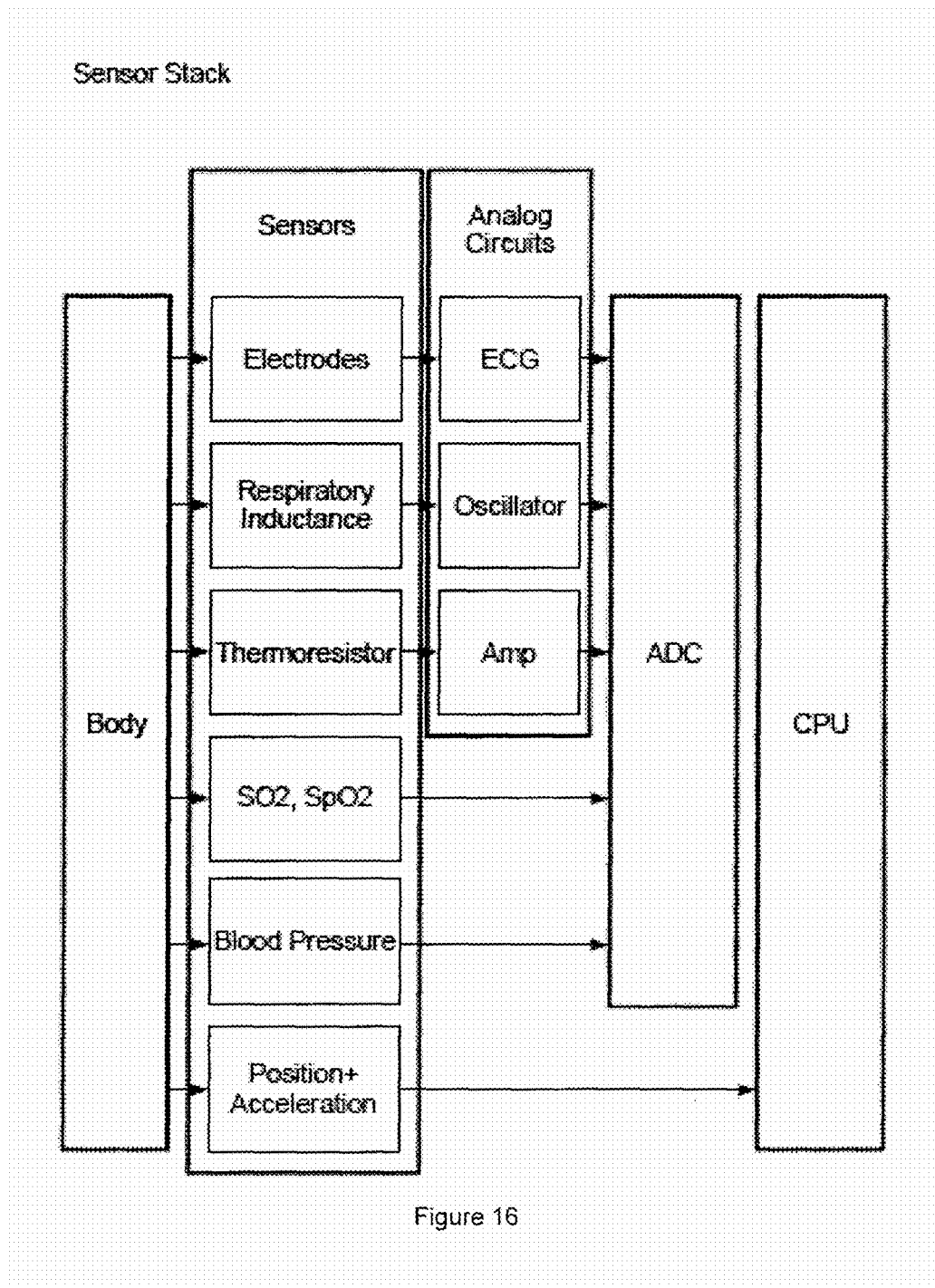
FIG. 16 shows a diagram of sensor front-end electronic module that can have the electronic device to process the analog physiological data, digitize the analog value using an analog to digital converter, and processing the physiological data using a CPU.
Figure 17:
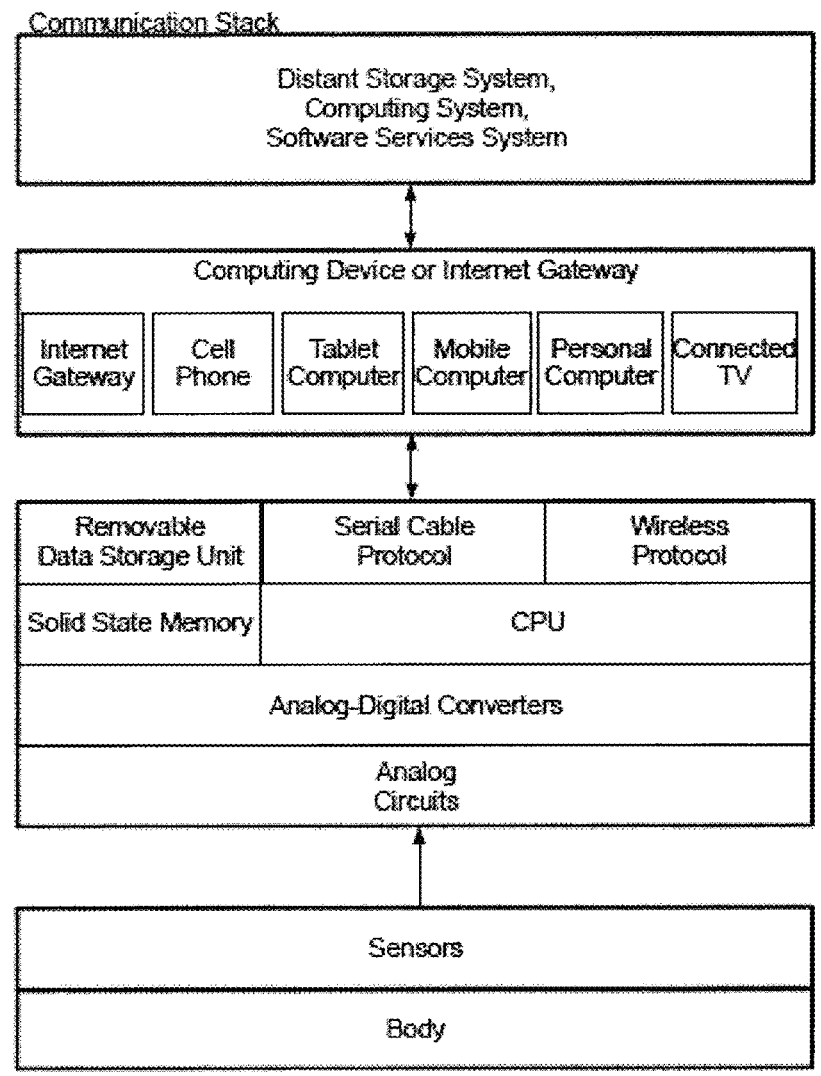
FIG. 17 shows a diagram of how the device can be used to record the physiological signals from the body sensors and transmit it first to any connected computing device that can be used to interpret the signals or an Internet gateway, and then to a distant computing and storage system.
Figure 19:
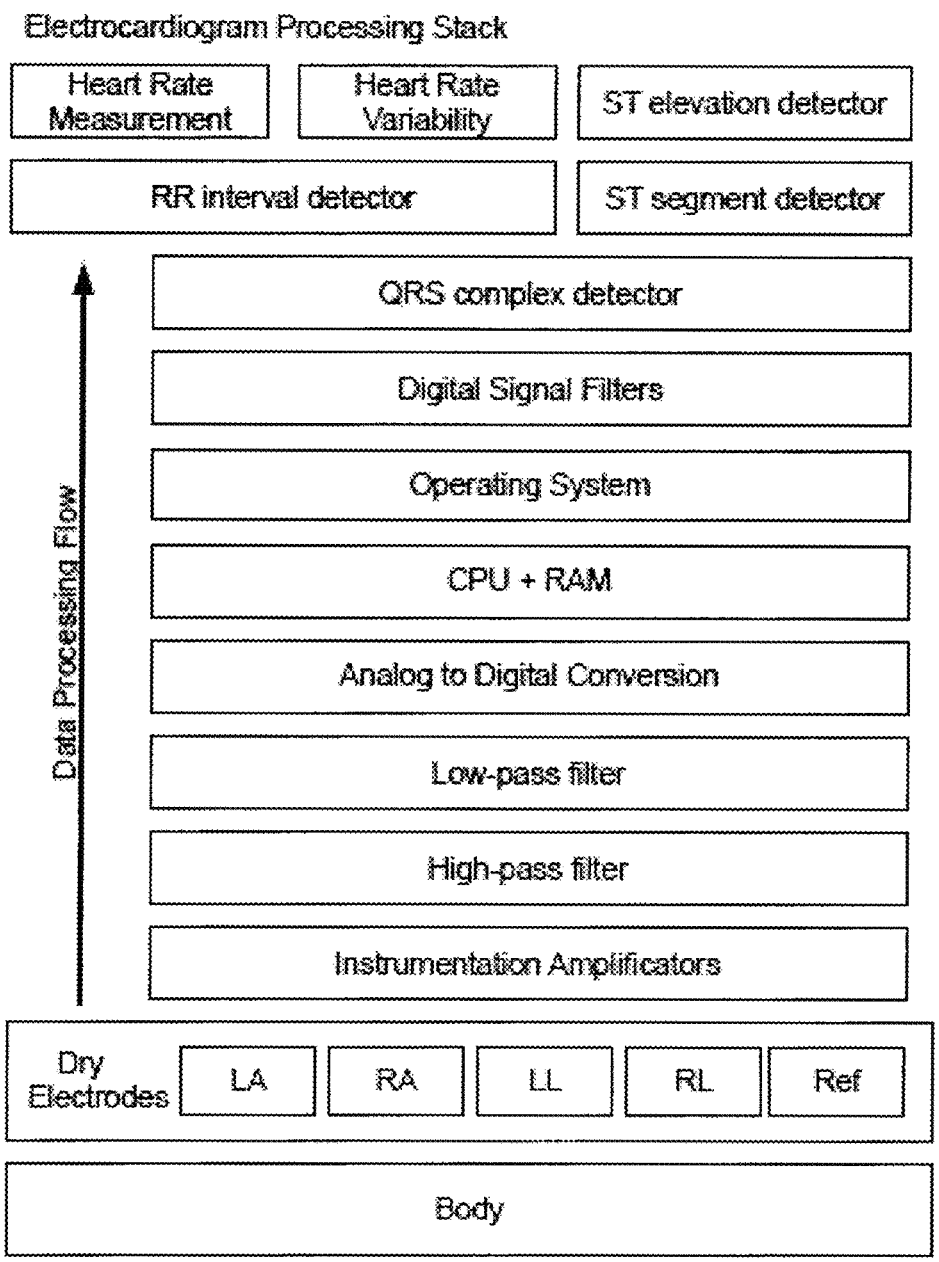
FIG. 19 shows a diagram of a physiological data processing flow, in this case the data coming from the electrocardiogram sensor.

In one example, the electronic device is further equipped with a button that can be used to record an event, initiate wireless pairing using a protocol like Bluetooth, or reset the device. In this example shown in FIG. 15, the device has 3 light emitting diodes used to communicate with users, for example to confirm to a wearer of the garment that the garment is connected, the electronic device is connected using a wireless link, a state of a battery of the electronic device, any malfunction or any other information the electronic device must communicate to the user. The electronic device may contain several analog and digital circuits to record and process the physiological signals as shown on FIG. 16. The electronic device can further implement all the normal functions of a computing device as shown on FIG. 18. The device can be connected to other computing and networking devices using a wired or wireless protocol as shown on FIG. 17, and can use another computing or networking device to communicate with a remote server, a distance storage system, or a distance computing system, which can provide automatic physiological data analysis services and help with the interpretation of physiological signals. For example, such an automatic physiological data analysis can be constructed using a stack of simple processing units to achieve a high-level understanding of the original physiological signal, such as detailed cardiac activity shown on FIG. 19, symptoms, and pathologies.

Although the present interconnection patch, male-female connector and washable intelligent garment have been described in the foregoing description by way of illustrative embodiments thereof, these embodiments can be modified at will, within the scope of the appended claims without departing from the spirit and nature of the appended claims.

What is claimed is:

1. A washable interconnection patch for receiving and interconnecting a plurality of wires to a cable, the patch comprising:
   two matching pieces interlocking together so as to define therebetween two opposite apertures, one of the apertures being adapted to receive and hold the plurality of wires and the other aperture being adapted to receive and hold the cable, an interior face of one of the two matching pieces defining a channel, the channel including a plurality of discrete connections;
   wherein, within the channel, each of the plurality of wires is connected to a corresponding one of the plurality of discrete interconnections; and
   wherein, within the channel, the plurality of discrete interconnections is connected to the cable.

2. The patch of claim 1, wherein one of the two matching pieces further comprises a fastening member for fastening the interlocked matching pieces to a fabric.

3. The patch of claim 1, wherein the two matching pieces are further adapted to be filled with a sealant.

4. A connection assembly comprising:
   a male connector, the male connector defining a series of independent connection points along a length thereof and having a resilient, curved extremity; and
   a female connector adapted to receive the male connector, the female connector defining along a length of an inner surface thereof a series of spring-loaded contact points;
   wherein the curved extremity of the male connector is configured to deflect the spring loaded contact points of the female connector during insertion of the male connector within the female connector until, when the male connector is fully inserted within the female connector, the connection points and the contact points are aligned and in contact together.

5. The assembly of claim 4, wherein:
   the male connector's cross section is shaped like a C and the connection points are located in a concave section thereof; and
   an entry of the female connector is C-shaped.

6. The assembly of claim 4 wherein:
   the male connector comprises electrical contacts plated with gold or another conductive material.

7. The assembly of claim 5, wherein the series of independent connection points of the male connector are part of a printed circuit board.

8. The assembly of claim 4, wherein the connection points and contact points are aligned in a direction of insertion of the male connector within the female connector.

9. The assembly of claim 4, wherein the connection points and contact points are electrical points.

10. The assembly of claim 4, wherein the male connector is adapted for use in a washable garment.

11. An intelligent washable garment, the garment comprising:
    a plurality of sensors, each of the sensors having a corresponding cable; and
    an electronic device for receiving signals generated by the plurality of sensors, the electronic device comprising:
      a casing,
      a connection assembly comprising a male connector and a female connector, the male connector defining a series of independent connection points along a length thereof and having a resilient, curved extremity, each of the connection points being electrically connected to one of the cables of the sensors, the female connector being adapted to receive the male connector, the female connector defining along a length of an inner surface thereof a series of spring-loaded contact points, wherein the curved extremity of the male connector is configured to deflect the spring loaded contact points of the female connector during insertion of the male connector within the female connector until, when the male connector is fully inserted within the female connector, the connection points and the contact points are aligned and in contact together and the signals received by the male connector from the sensors are transferred to the female connector, and
      a processing unit in electrical communication with the female connector for processing the signals received by the female connector.

12. The garment of claim 11, wherein the processing unit is capable of recording physiological signals automatically.

13. The garment of claim 12, wherein the electronic device starts recording the physiological signals automatically from the sensors upon complete connection of the male connector within the female connector, and stops recording when the male connector is removed from the female connector.

14. The garment of claim 1, wherein each of the two matching pieces extend from the one of the apertures adapted to receive and hold the plurality of wires to the other aperture adapted to receive and hold the cable.

* * * * *